(12) United States Patent (10) Patent No.: US 11,231,366 B2
Mueller et al. (45) Date of Patent: Jan. 25, 2022

(54) METHOD AND DEVICE FOR DETERMINING A GLOSS VALUE OF HAIR (71) Applicant: Henkel AG & Co. KGaA, Duesseldorf (DE)

(72) Inventors: Burkhard Mueller, Duesseldorf (DE); Torsten Lechner, Langenfeld (DE)

(73) Assignee: HENKEL AG & CO. KGAA, Duesseldorf (DE)

(*) Notice: Subject to any disclaimer, the term of this patent is extended or adjusted under 35 U.S.C. 154(b) by 0 days.

(21) Appl. No.: 16/641,777

(22) PCT Filed: Jul. 27, 2018

(86) PCT No.: PCT/EP2018/070378
§ 371 (c)(1),
(2) Date: Feb. 25, 2020

(87) PCT Pub. No.: WO2019/048128
PCT Pub. Date: Mar. 14, 2019

(65) Prior Publication Data
US 2020/0249161 A1 Aug. 6, 2020

(30) Foreign Application Priority Data
Sep. 7, 2017 (DE) .................... 10 2017 215 791.7

(51) Int. Cl.
*A45D 44/00* (2006.01)
*G01N 21/57* (2006.01)
(Continued)

(52) U.S. Cl.
CPC ............. *G01N 21/57* (2013.01); *A45D 44/00* (2013.01); *G01N 33/4833* (2013.01);
(Continued)

(58) Field of Classification Search
CPC ........... G01N 21/57; G01N 2201/0221; A45D 44/00; A45D 2204/007; G06Q 30/0631; G06Q 30/0633
(Continued)

(56) References Cited

U.S. PATENT DOCUMENTS 6,333,985 B1 * 12/2001 Ueda .................... A45D 44/005
382/100
6,723,308 B2 * 4/2004 Browning .............. A61K 8/362
424/401

(Continued)

OTHER PUBLICATIONS

N Lefaudeux et al New luster formula for the characterization of hair tresses using polarization imaging Journal of Cosmetic Science Mar. 1, 2009 Mar. 1, 2009 United States pp. 153 169 XP055147578 Retrieved from the Internet URLhttpwwwncbinlmnihgovpubmed19450417 DOI 101111j14682494201000534_7x (Year: 2009).*
(Continued)

*Primary Examiner* — Alexis M Casey
(74) *Attorney, Agent, or Firm* — Lorenz & Kopf, LLP (57) ABSTRACT

In various exemplary embodiments, a device for determining the gloss value of hair is provided. The device includes a light source for illuminating at least one hair with light, where the at least one hair is arranged to extend along a cylinder section-like carrier in such a way that a plurality of adjacent hair sections is arranged essentially perpendicular to a cylinder axis. The device further includes a portable camera for capturing a digital image of the at least one hair during illumination and a portable electronic data processing device for determining a gloss value of the hair based on the digital image.

14 Claims, 7 Drawing Sheets

(51) Int. Cl.
*G01N 33/483* (2006.01)
*G06Q 30/06* (2012.01)

(52) U.S. Cl.
CPC ..... *G06Q 30/0631* (2013.01); *G06Q 30/0633* (2013.01); *A45D 2044/007* (2013.01); *G01N 2201/0221* (2013.01)

(58) Field of Classification Search
USPC ....................................................... 705/26.7
See application file for complete search history.

(56) References Cited

U.S. PATENT DOCUMENTS

| | | | | |
|---|---|---|---|---|
| 7,226,585 B2* | 6/2007 | Browning | ............... | A61K 8/362 |
| | | | | 424/401 |
| 8,428,382 B2* | 4/2013 | Sato | .................... | A45D 44/005 |
| | | | | 382/254 |
| 8,484,155 B2* | 7/2013 | Yamaguchi | ............ | A61B 5/448 |
| | | | | 706/54 |
| 10,231,531 B2* | 3/2019 | Witchell | ................ | G01N 21/31 |
| 10,379,032 B2* | 8/2019 | Godfrey | .................... | G06T 7/90 |
| 2007/0100555 A1* | 5/2007 | Ladjevardi | ............. | G16H 20/70 |
| | | | | 702/1 |
| 2014/0313302 A1* | 10/2014 | Franke | ................. | A45D 44/005 |
| | | | | 348/77 |
| 2017/0206678 A1* | 7/2017 | Kowalczyk | .......... | G06K 9/6212 |

OTHER PUBLICATIONS

Kaplan et al The shine problem in hair Review of imaging methods and measures for luster vol. 60 No. 2 Mar. 1, 2009 Mar. 1, 2009 pp. 111 123 XP009503908 ISSN 15257886 Retrieved from the Internet URLhttpjournalsccconlineorgcontentscc2009cc060n02html (Year: 2009).*

Journal of Cosmetic Science McMullen R Jachowicz J 335351 (Year: 2002).*

* cited by examiner

METHOD AND DEVICE FOR DETERMINING A GLOSS VALUE OF HAIR

CROSS-REFERENCE TO RELATED APPLICATION

This application is a U.S. National-Stage entry under 35 U.S.C. § 371 based on International Application No. PCT/EP2018/070378, filed Jul. 27, 2018, which was published under PCT Article 21(2) and which claims priority to German Application No. 10 2017 215 791.7, filed Sep. 7, 2017, which are all hereby incorporated in their entirety by reference.

TECHNICAL FIELD

The present disclosure concerns a method and device for determining a gloss value of hair and a method for determining a hair care product and/or a hair treatment recommendation.

BACKGROUND

Shiny, healthy looking hair may be an important cosmetic goal, which may be achieved by using cosmetic products to increase the gloss.

The suitability of a gloss enhancement product for a hair type may depend on whether the hair is already very shiny or not, in other words on the gloss value of the hair.

Users often do not know which gloss enhancement products are best suited for their hair type (e.g. their current hair gloss value) to create shiny(er) hair. One reason for this may be that they do not have a way to objectively assess their hair gloss value. Sometimes, in order to distinguish the hair gloss value before application of a hair gloss product and a hair gloss value after application of the hair gloss product, the hair gloss value before application is also called original hair gloss value, initial hair gloss value, or starting hair gloss value.

Another reason why users often do not know which gloss enhancement products are suitable for them may be that the products are not labeled with information about which initial hair gloss value they are suitable for.

Therefore, there is a need for a quantitative evaluation of a hair gloss. It would also be desirable to have a simple applicability with little or no equipment, so that the hair gloss value may also be determined by a user, for example.

Furthermore, there is a need to obtain a product recommendation for a gloss enhancement product which is suitable for an initial hair gloss value of a user.

SUMMARY

A method for determining a gloss value of hair is provided herein. The method comprises illuminating at least one hair with light, wherein the at least one hair is arranged to extend along a cylinder section-like support in such a way that a plurality of adjacent hair sections is arranged essentially perpendicular to a cylinder axis; during illumination, capturing a digital image of the at least one hair by a portable camera, and determining a gloss value of the hair based on the digital image.

A device for determining a gloss value of hair is also provided. The device comprises a light source for illuminating at least one hair with light, wherein the at least one hair is arranged extending along a cylinder section-like carrier in such a way that a plurality of hair sections arranged side by side are essentially perpendicular to a cylinder axis; a portable camera for capturing a digital image of the at least one hair during illumination, and a portable electronic data processing device for determining a gloss value of the hair based on the digital image.

In various exemplary embodiments, the device and the method for determining a hair gloss value are provided by an external, preferably mobile light source, which takes an image of hair in which the hair may be curved in a defined radius around a cylindrical object (e.g. a curler).

Depending on the length of the hair, one hair may be sufficient. Usually at least about 5 hairs, preferably at least about 10 hairs may be used.

In various exemplary embodiments, hair lying close on the head may be sufficiently curved for the method to be applied, so that an object for curling up the hair is not necessary.

In various exemplary embodiments, a perfectly circular object may be used as the cylindrical object. This means that a ratio of the largest and smallest radius of the cylinder is as close as possible to one.

The gloss value may be determined in various exemplary embodiments using conventional methods.

In various exemplary embodiments, the hair may be illuminated with light. Since the hair may be arranged on the cylinder, there may be different angles between the light source and the hair surface, and also angle-dependent reflection or scattering intensities.

While illuminating the hair with light, a digital image of the hair may be taken in various exemplary embodiments.

In various exemplary embodiments, a method for determining the gloss value may be used, which may be based on a method by Reich-Robbins, whereby a proportion of diffuse scattering in the digital image may be determined approximately from a signal intensity at angles close to about 45° and subtracted from a total signal. The gloss results from a ratio of gloss reflection and scatter as well as a gloss bandwidth.

In various exemplary embodiments, a method for determining the gloss value according to Lefaudeux et al. ("New luster formula for the characterization of hair tresses using polarization imaging", Third Annular Conference on applied Hair Science, September 2008) or a technology used by Bossa Nova (http://www.bossanovatech.com/samba_hair_system_technology.htm) may be used.

The light with which the hair is illuminated may be polarized light in various exemplary embodiments.

In various exemplary embodiments, the camera by which the digital image is taken may be a digital camera of a smartphone, tablet or phablet.

In various exemplary embodiments, the light source by which the hair is illuminated may be a light source of a smartphone, tablet or phablet. In such a case, in various exemplary embodiments, the polarized light may be provided by an attachment for the smartphone, tablet, etc., for example, a CPL polarizing filter attachment by Memteq.

In various exemplary embodiments, the latter method may be used to distinguish between a reflection from the front and a reflection from the rear of the hair.

In various exemplary embodiments, calibration measurements may be performed on hair with known gloss values. The results of the calibration measurements may be grouped into gloss levels in various exemplary embodiments and entered into a database. For each gloss level, a corresponding product recommendation may be entered into the database in various exemplary embodiments.

In case of low gloss levels, products that greatly increase the hair gloss may be recommended in various exemplary embodiments. For high gloss levels, various exemplary embodiments may recommend products that moderately increase the hair gloss.

In various exemplary embodiments, a method is provided to determine the gloss value of hair, which may for instance be quantified as a gloss level.

The determined gloss value may be used in various exemplary embodiments to determine a gloss enhancement product recommended for hair with the determined gloss value.

In various exemplary embodiments, the determination of the gloss value may be used to determine the success of a hair treatment for gloss enhancement.

A digital image on which hair is depicted may be taken in various exemplary embodiments using a digital camera.

While the image is being captured, the hair, which may be curved along an essentially cylindrical surface, may be or is illuminated with light, e.g. polarized light, in various exemplary embodiments.

In various exemplary embodiments, the essentially cylindrical surface may be a surface of a essentially cylindrical object or at least a part thereof.

In various exemplary embodiments, the essentially cylindrical surface may be a surface of the user's head or at least a part thereof.

In various exemplary embodiments, the method may be executable with little or no technical effort. For example, the method may be executed using an app on a tablet or smartphone. This may enable a user, for example, to determine the gloss value of a hair, e.g. his hairstyle, without professional support and without having to provide a hair sample for manipulation in the laboratory, for example by using a smartphone or tablet to capture a digital image of hair arranged in the curvature described (which may already be present in hair running along the surface of the user's head) and to determine the smoothness value by the smartphone/tablet, e.g. by an app provided in the smartphone/tablet. In various exemplary embodiments the smartphone/tablet may be used to provide the image of an external data processing device, e.g. a processor cloud architecture (also referred to as cloud), and to receive and display the results determined there to the user.

In various exemplary embodiments, a user may receive an exact product recommendation tailored to his initial hair gloss, e.g. for increasing hair gloss, without having to carry out his own hair assessment, but simply by taking or having taken one or more pictures of his hair with his smartphone and having them evaluated by an app for determining a hair care product and/or a hair treatment recommendation.

In various exemplary embodiments, a method for determining a gloss value of hair is provided. The method may comprise illuminating at least one hair with light, wherein the at least one hair may be arranged to extend along a cylinder section-like carrier in such a way that a plurality of adjacent hair sections is positioned essentially perpendicular to a cylinder axis, taking a digital image of the at least one hair by a portable camera during illumination and determining a gloss value of the hair based on the digital image.

In various exemplary embodiments, the light may be linearly polarized, wherein an oscillation plane of the polarized light may be along the cylinder axis.

In various exemplary embodiments, determining the gloss value of the hair may include determining a maximum brightness value in a hair area of the digital image and assigning the maximum brightness value to a gloss value.

In various exemplary embodiments, determining the gloss value of the hair may involve determining a gloss range in a hair area of the digital image and summing gloss brightness values of all image elements in the gloss range and assigning the sum to a gloss value.

In various exemplary embodiments, the method may further comprise positioning the portable camera in such a way that an angle between a main direction from which the light illuminates the hair and an optical axis of the camera forms an angle of approximately 45°.

In various exemplary embodiments, the illumination of at least one hair may be performed by a light source, which together with the camera is part of an integrated portable device.

In various exemplary embodiments, the method may further comprise arranging the hair on a cylinder-like body.

In various exemplary embodiments, the digital image may be parameterized in a color space that includes brightness as one parameter.

In various exemplary embodiments, a method for determining a hair care product and/or a hair treatment recommendation is provided. The method may include a determination of a gloss value of hair according to various exemplary embodiments and a determination of a hair care product and/or a hair treatment recommendation for gloss enhancement based on the determined gloss value.

In various exemplary embodiments, a device for determining a gloss value of hair is provided. The device may comprise a light source for illuminating at least one hair with light, wherein the at least one hair may be positioned along a cylinder section-like carrier in such a way that a plurality of adjacent hair sections is positioned essentially perpendicular to a cylinder axis, a portable camera for taking a digital image of the at least one hair during illumination, and a portable electronic data processing device for determining a gloss value of the hair based on the digital image.

In various exemplary embodiments, the camera and the data processing device may be part of an integrated portable device.

In various exemplary embodiments, the light source may be part of the integrated portable device.

In various exemplary embodiments, the integrated portable device may be a smartphone, a tablet or a phablet.

In various exemplary embodiments, the light emitted by the light source may be linearly polarized light.

In various exemplary embodiments, the gloss value may have a value from a multi-level gloss value scale which may include gloss values from very low to very high, wherein the hair care product for gloss enhancement may be one of a plurality of hair care products for gloss enhancement, wherein each of the plurality of hair care products for gloss enhancement is assigned a gloss enhancement level, wherein determining a hair care product based on the determined gloss value comprises determining a hair care product with a higher gloss generation level for hair with a lower gloss value.

In various exemplary embodiments, capturing the at least one digital image may comprise capturing a plurality of digital images, wherein each image may represent a hairstyle from a different viewing direction.

In various exemplary embodiments, determining the gloss value of hair may involve determining a common hairstyle gloss value based on the plurality of gloss values from the plurality of digital images.

In various exemplary embodiments, determining a gloss value of hair based on the digital image may include determining a hair display area in which the at least one hair of the user is displayed.

In various exemplary embodiments, the determination of a gloss value of the hair based on the digital image may also involve defining the entire hair display area as the hair examination area.

In various exemplary embodiments, the method may further include an output of the determined gloss value and/or the determined hair care product.

In various exemplary embodiments, the output of the determined gloss value and/or the determined hair care product may include representation by a display device.

BRIEF DESCRIPTION OF THE DRAWINGS

The present disclosure will hereinafter be described in conjunction with the following drawing figures, wherein like numerals denote like elements, and.

FIG. is 1B a graphical illustration of a device for determining a gloss value of hair according to various exemplary embodiments, wherein the application of a method for determining a gloss value of hair according to various exemplary embodiments is illustrated.

FIGS. are 2A and 2B respectively digital images captured by a device for determining a gloss value of hair according to various exemplary embodiments, or in performing a method for determining a gloss value of hair according to various exemplary embodiments.

FIG. is 3 a brightness curve obtained by applying a method for determining a gloss value of hair according to various exemplary embodiments.

FIG. is 4 a flow chart of a method for determining a gloss value of hair according to various exemplary embodiments.

DETAILED DESCRIPTION

In the following detailed description, reference is made to the attached drawings which form part of the present application and in which, by way of illustration, specific embodiments are shown in which the present disclosure may be carried out. In this respect, directional terminology such as "top", "bottom", "front", "back", "forward", "backward", etc. is used in relation to the orientation of the Figure(s) described. Since components of exemplary embodiments may be positioned in a number of different orientations, the directional terminology is used for illustration purposes and is not restrictive in any way. It goes without saying that other exemplary embodiments may be used and structural or logical changes may be made without deviating from the scope of protection of the present disclosure. Furthermore, it goes without saying that the features of the various exemplary embodiments described herein may be combined, unless specifically stated otherwise. The following detailed description is therefore not to be understood in a restrictive sense and the scope of protection of the present disclosure is defined by the attached Claims.

A digital image may herein be understood to be a data packet which may be represented by a data processing system as a two-dimensional (planar) arrangement of pixels, for example in a coordinate system having an x-axis and a y-axis, each pixel having at least one image position as an x,y coordinate pair and an intensity information, the intensity information being representable for example as the color of a pixel of a monitor or a printed dot of a printed image. In a color image, the intensity information may refer to individual color channels. The digital image may be, for example, a photograph taken with a digital camera or a single frame of a video sequence taken with a digital camera.

In the case of a smartphone referred to herein, unless the context indicates otherwise, this is to be understood as representative of all similar types of portable data processing device, i.e. smartphones, tablets, phablets, laptops, etc. The same applies to smartphone cameras and the like.

Figure 1A:
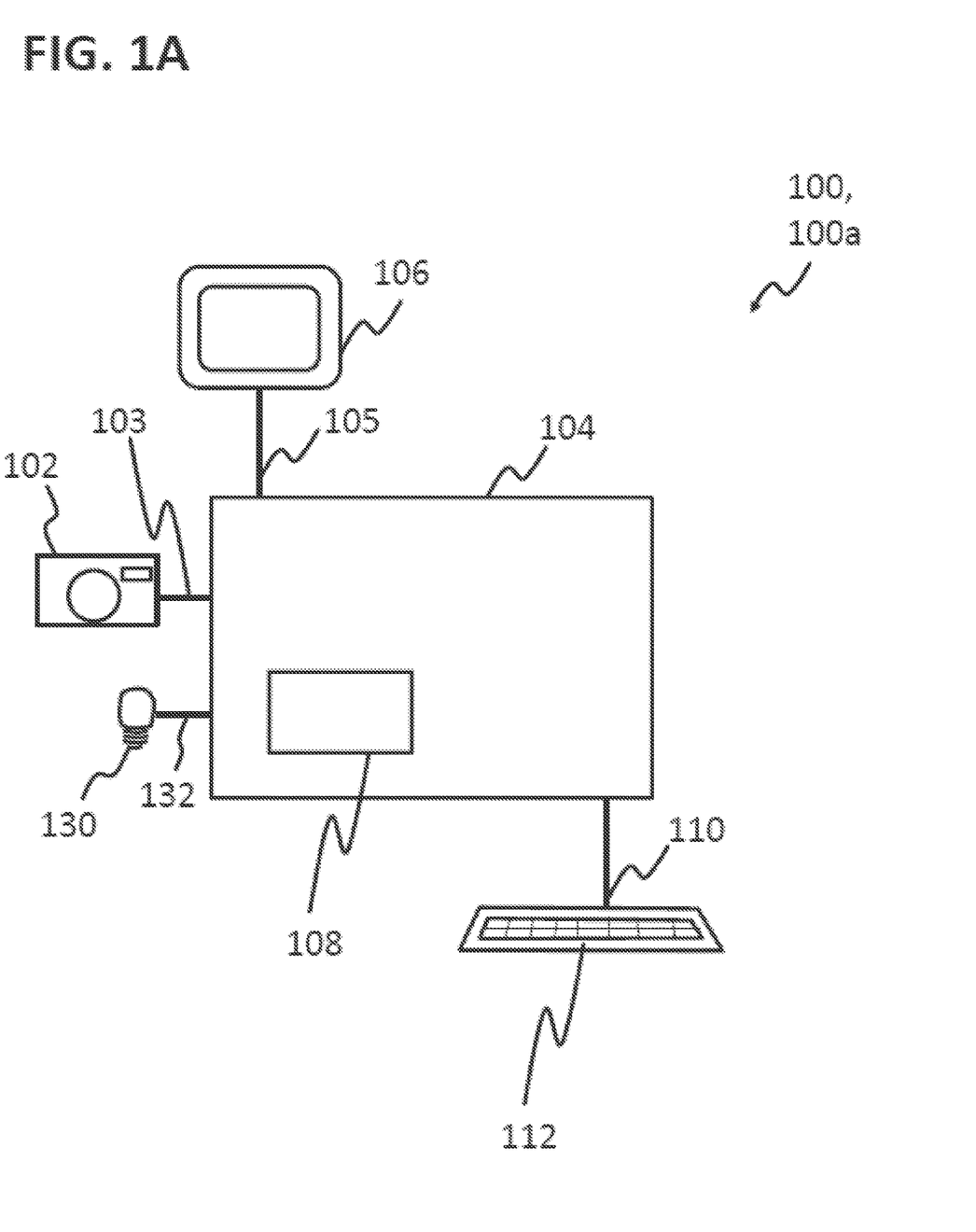
FIG. 1A is a graphical illustration of a device for determining a gloss value of hair according to various exemplary embodiments.
Figure 1B:
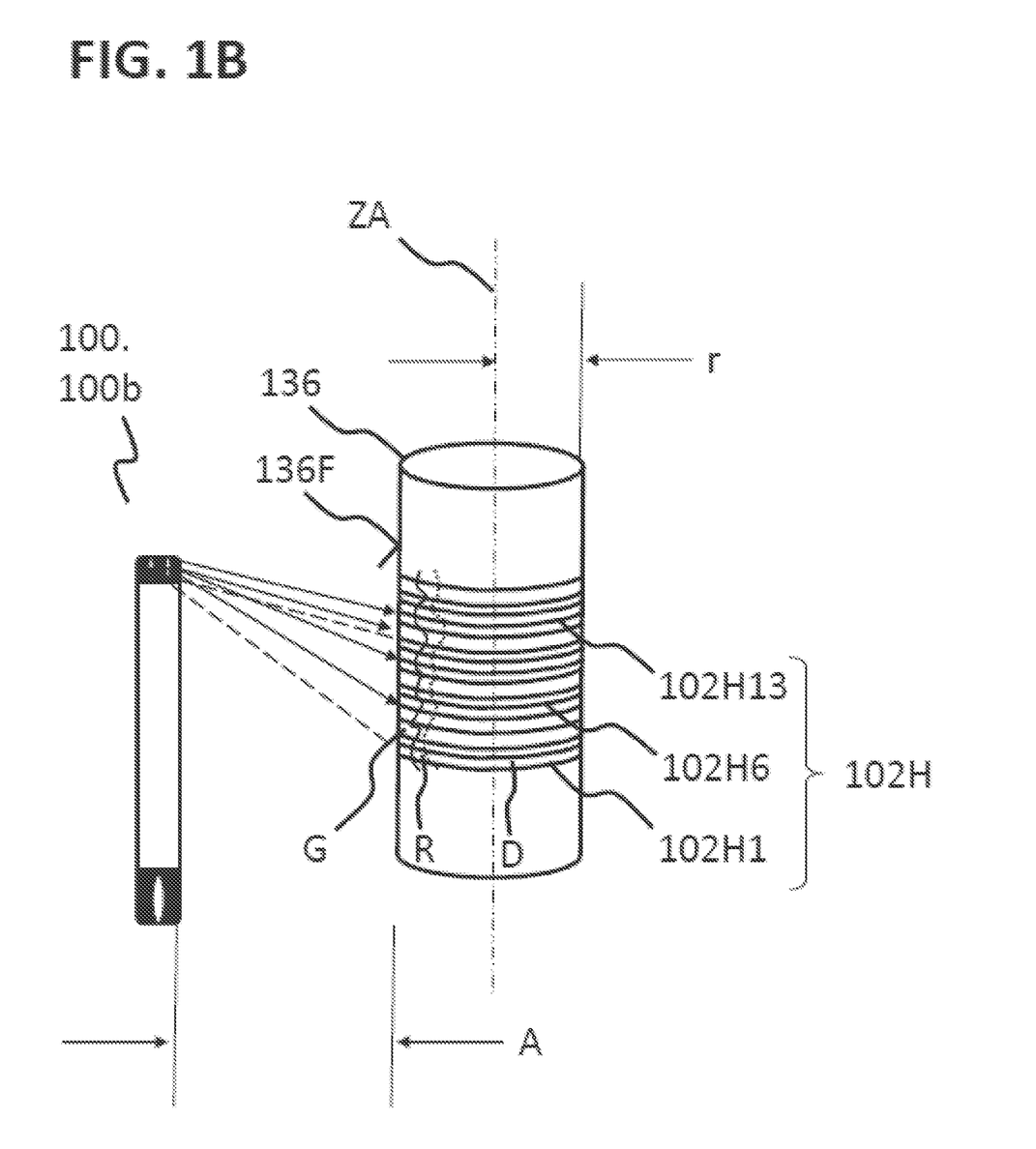

FIG. 1A shows a graphical illustration of a device 100, 100a for determining a gloss value of hair according to various exemplary embodiments, and FIG. 1B shows a graphical illustration of a device 100, 100b for determining a gloss value of hair according to various exemplary embodiments, wherein applying a method for determining a gloss value of hair according to various exemplary embodiments is illustrated. The device 100 may further be set up to determine a hair care product and/or a hair treatment recommendation according to various exemplary embodiments.

In various exemplary embodiments, the device 100 may comprise a portable data processing device 104 for determining a gloss value of hair or for determining a hair care product and/or a hair treatment recommendation. The portable data processing device 104 may comprise, for example, a tablet, a smartphone, a laptop.

The portable data processing device 104 may be equipped to perform a method for determining a gloss value of hair or for determining a hair care product and/or a hair treatment recommendation according to various exemplary embodiments. The data processing device 104 may comprise a processor 108, for example a microprocessor.

In various exemplary embodiments, the device 100 for determining a gloss value of hair or for determining a hair care product and/or a hair treatment recommendation may include an output device 106, e.g. a display device. Instead of the display device or in addition to the display device, a different type of output device, e.g. a loudspeaker, may be provided in various exemplary embodiments.

The output device 106, e.g. a display device, may, for example, include a (e.g. touch-sensitive) screen of a smartphone, laptop or tablet. The output device 106, e.g. a display device, may be used to present results of the method for determining a gloss value of hair or for determining a hair care product and/or a hair treatment recommendation, e.g. the determined gloss value and/or the determined care product, to request input parameters for carrying out the method, or the like.

The output device 106, e.g. a display device, may be connected to the data processing device 104 by a first data link 105. The output device 106, e.g. a display device, may exchange data with the data processing device 104 via the first data link 105. In a case where the device 100 comprises a smartphone, tablet or the like, the output device 106, e.g. a display device, and the first data link 105 may be integrated in the device 100 as shown in FIG. 1B for the device 100b.

In various exemplary embodiments, device 100 may include a camera 102 for determining a gloss value of hair or for determining a hair care product and/or a hair treatment recommendation.

The camera 102 may be set up according to various exemplary embodiments, to take a digital image 200 of hair 102H, e.g. of a user's hair, as described elsewhere.

The one camera 102 may be equipped with a digital photo camera of a smartphone, tablet, etc. according to various exemplary embodiments. In this case, the camera may be integrated in the device 100, as shown in FIG. 1B for the device 100b.

In various exemplary embodiments, the device 100 for determining a gloss value of hair or for determining a hair care product and/or a hair treatment recommendation may include a second data link 103 between the data processing device 104 and the camera 102. By the second data link 103, data may be transmitted from the data processing device 104 to the camera 102, e.g. for conventional software control of the camera 102. In addition, the second data link 103 allows data, such as the digital image(s) captured by the camera 102, to be transmitted to the data processing device 104. In a case where the device 100 includes a smartphone, tablet, etc., the camera 102 and the second data link 103 may be integrated in the device 100.

The data processing device 104 may be configured, for example, using the processor 108, to process the image received from the camera 102 by image processing software, for example to determine in a known manner the hair display area in the received image and, as described elsewhere herein for various exemplary embodiments, to determine the gloss value of hair by essentially known methods, for example by employing a Reich-Robbins method or, for example, by a method according to Lefaudeux et al. The image processing software may include an app in various exemplary embodiments.

In various exemplary embodiments, the device 100 may include an input device 112 for providing information to the data processing device 104, for example a touch-sensitive surface of the output device 106, a keyboard, a mouse or similar.

The input device 112 may be connected to the data processing device 104 by a third data link 110. The input device 112 may exchange data with the data processing device 104 via the third data link 110. In a case where the device 100 includes a smartphone, tablet or the like, the input device 112 and the third data link 110 may be integrated in the device 100. The device 100 may include a light source 130 in various exemplary embodiments. The light source may, for example, include an integrated lamp/light source (e.g. LED) of a smartphone, tablet or the like, or an external light source which may be controlled by the data processing device 104 via data link 132. In various exemplary embodiments, the light source may be switched on without being controlled by the data processing device (e.g. manually) to illuminate the hair 102H while the image is being captured.

In various exemplary embodiments, the light source 130 may be used to emit linearly polarized light. In the case of a smartphone lamp or other lamp which does not actually emit linearly polarized light, an additional device, e.g. an attachment (e.g. as described above), may be used to linearly polarize the light.

FIG. 1B shows an exemplary embodiment where the device 100, 100b is used to perform the method of determining the gloss value of hair according to various exemplary embodiments.

The device 100b includes as an integrated device 100b (a smartphone is shown as an example, a tablet, phablet or similar device could be used instead), the data processing device 104 with the processor 108, the camera 102, the display device 106, the input device 112 and the light source 130.

In order to create an evaluable gloss effect on illuminated hair 102H, it may be necessary to arrange hair 102H in such a way that individual hairs or at least hair sections 102H1, . . . , 102H6, . . . , 102H13, . . . (as shown in FIG. 1B) are arranged essentially parallel to each other and with a curvature.

In FIG. 1B this is achieved by wrapping at least one hair 102H around a cylindrical object 136, e.g. a curler. When using the cylinder-like object, a circular cylinder may be used, i.e. a cylinder with a circular base. As an alternative, a cylinder with an elliptic base may be used, e.g. with a base where a ratio of a largest radius to a smallest radius of the cylinder is in a range of about 1.01 to about 1.3.

Using a standardized cylinder-like object, for example with a defined size and radius of curvature (and thus a curved surface 136F, on which the hairs 102H are arranged, and a straight cylinder axis ZA), may lead in various exemplary embodiments to more uniform absolute values of brightness values to be determined from the captured image.

Figure 2A:
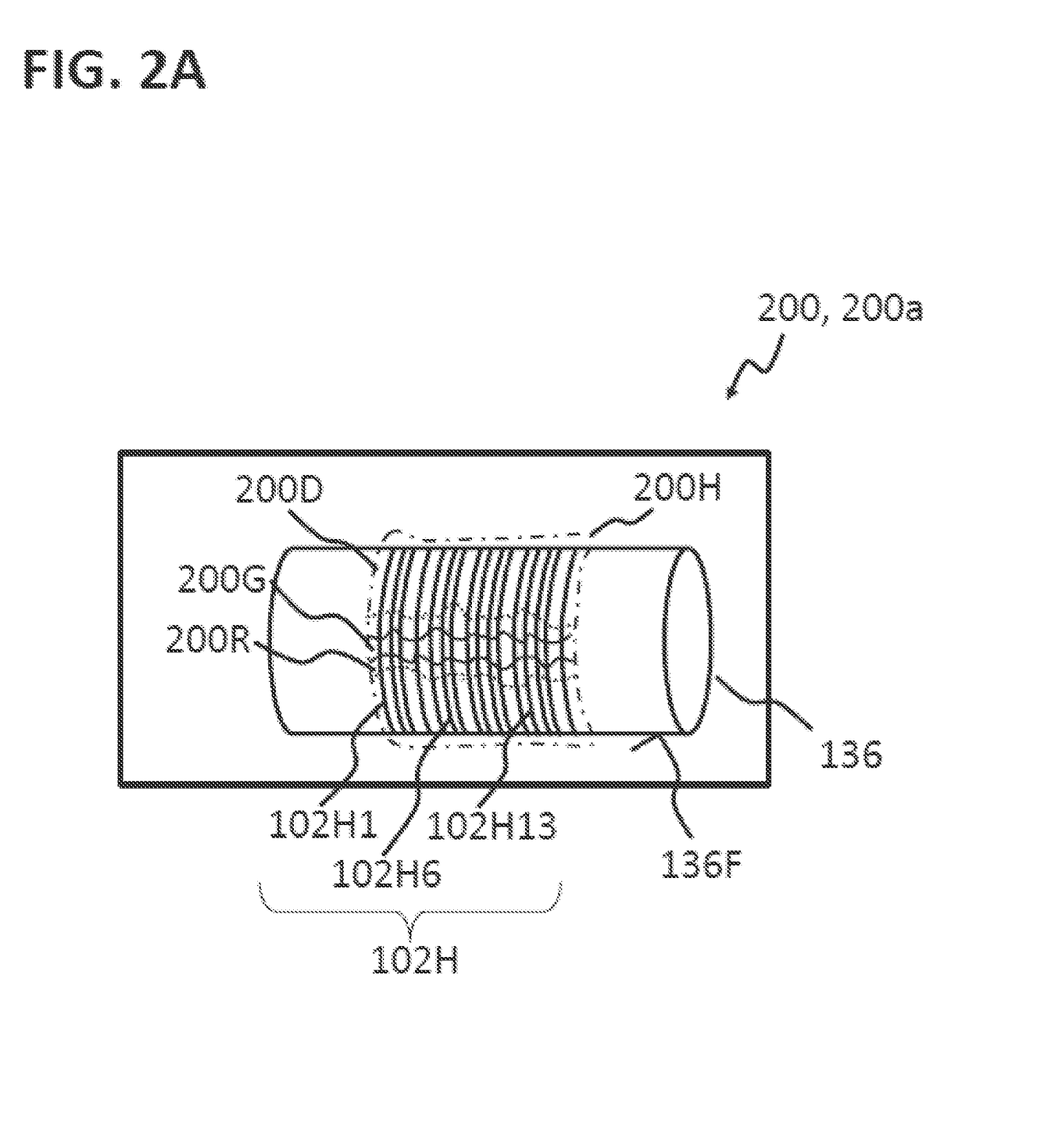
Figure 2B:
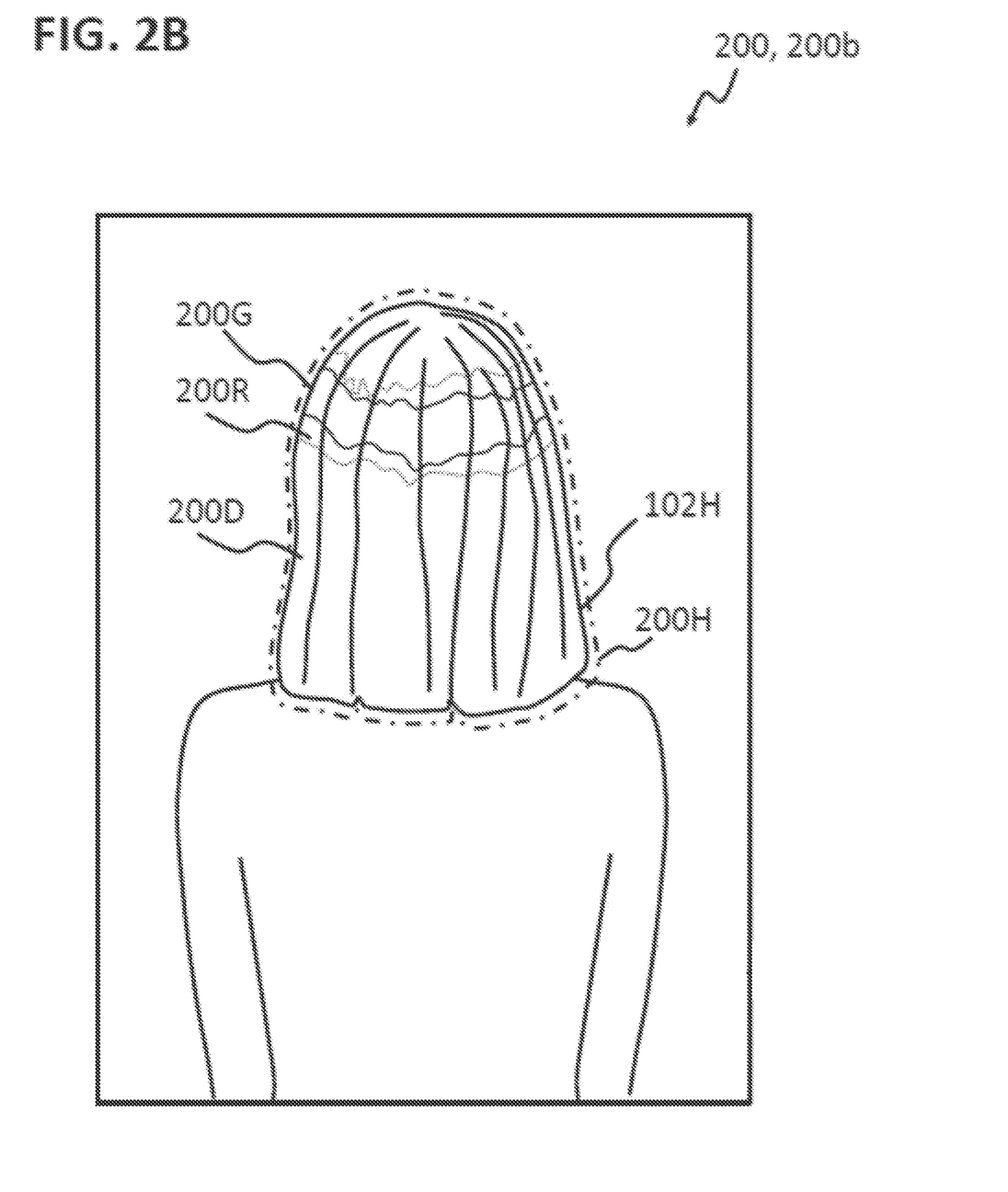

An easier implementation of the method in various exemplary embodiments may be achieved by using non-standard curved surfaces 136F, for example, as shown in FIG. 2B, a curved head surface. The "cylinder axis" or, alternatively, a vertex of the radius of curvature facing the light source may run along a curved line instead of being exactly straight as in the cylindrical object 136.

For example, to create the hair arrangement of FIG. 1B, the user may have hairs 102H cut off, e.g. between about 5 and about 1000 hairs 102H, e.g. between about 10 and about 50, e.g. about 30. Alternatively, the hairs 102H may be left on the head for further execution of the method provided they are long enough.

The hairs 102H may be arranged on the (e.g. exactly circular) cylinder (e.g. a plastic cylinder) so that they are all stretched or essentially stretched, exactly or essentially parallel to each other.

By the device 100b (e.g. the smartphone 100b) the hairs 102H may be illuminated and a photo taken at the same time.

For an evaluation, an arc of about 90° of the cylinder may be used in the example.

In various exemplary embodiments, the described arrangement and execution may lead to an angle-dependent light reflection, which shows reflected and scattered light, e.g. includes reflected light.

In various exemplary embodiments, the determination of the gloss value on the hair may be carried out using software installed in the smartphone, e.g. an app, according to Reich-Robbins or another known method.

In various exemplary embodiments, a light intensity with which the hair 102H is illuminated may be included in the evaluation. In various exemplary embodiments, a light intensity of the light source may be included, for example, based on known technical data of the light source 130.

In various exemplary embodiments, a distance A between the light source 130 and the at least one hair 102H of user may also be used. The distance A may, for example, be predetermined, be determined from the image (e.g. from an apparent size of the head or cylindrical object 136) or be measured by an additionally provided (not shown) distance measuring device.

FIGS. 2A and 2B each show digital images 200 (200a or 200b) taken by a device for determining a gloss value of hair according to various exemplary embodiments or when performing a method for determining a gloss value of hair according to various exemplary embodiments, for example by one of the devices 100 of FIG. 1A or FIG. 1B.

The image 200, in which at least one hair 102 of the user is represented, has been taken by a method for determining the gloss value of hair according to various exemplary embodiments and is intended for determining the gloss value or a hair care product.

In various exemplary embodiments, the digital image 200 may be, for example, a so-called black-and-white image, which only contains brightness information, for example a grayscale image, in which white may be assigned a maximum brightness and black a minimum brightness.

In various exemplary embodiments, the digital image 200 may be a color image 200 encoded in a color space (e.g. L*a*b*) with a plurality of parameters, one of the parameters being a brightness. For carrying out the method described herein, e.g. for determining the gloss value, an examination of the image in various exemplary embodiments may be or become limited to the brightness parameter. In various exemplary embodiments, a color may be included in the examination.

In various exemplary embodiments, the image 200 may be provided as an image parameterized in a color space that has no brightness parameter, e.g. RGB. For example, the image 200 may be transformed into a color space that has a brightness parameter, e.g. L*a*b*. For a subsequent examination to determine the gloss value of hair only the brightness parameter may then be used in various exemplary embodiments and the other parameters (e.g. hue, saturation) ignored. In various exemplary embodiments, the other parameters (e.g. hue, saturation) may be included or ignored in the examination.

In various exemplary embodiments, in image 200, regardless of whether in image 200 the hairs 102H are curved on the user's head as in FIG. 2B or, for example, one or more hairs 102H on the curved surface 136F of the essentially cylindrical (e.g. cylindrical or circular) object 136 (which hairs 102H may still be attached to or removed from the head of the user) as shown in FIGS. 1B and 2A, a hair display area 200H is determined in which the at least one hair 102H, e.g. the hairs 102H (e.g. main hair, i.e. without eyebrows, beard, etc.) is/are represented. In FIG. 2A and FIG. 2B, the hair display area 200H is shown slightly beyond the actual hair display area 200H for better recognition.

Hair display area 200H may contain a number of pixels from digital image 200 that represent hair 102H and that may form a continuous area or an area including a number of individual areas. For example, a plane in which the hair display area may be located may be defined by the x-axis and y-axis of the digital image 200.

In various exemplary embodiments, the digital image 200 may include other display areas in addition to the hair display area 200H, in which objects, body parts, etc. may be displayed.

In various exemplary embodiments, an examination of the digital image 200 to determine the gloss value, e.g. with regard to brightness values, may be limited to a hair examination area instead of extending to an entire image area. In various exemplary embodiments, the hair examination area may be selected in such a way that no part of the other display areas falls within the hair examination area, e.g. limited to the hair display area 200H.

In image 200, differently bright areas 200G, 200R and 200D may be determined in curved areas of hair 102H, in which the light has interacted differently with hair 102H in each case: in the glossy area 200G it was mainly reflected from a front of hair 102H, in the marginal area 200R from a back of hair 102H (after passing through the hair), and in a diffuse area 200D it was mainly scattered. Corresponding light components are marked G, R and D in FIG. 3.

A ratio of intensities of the reflected fractions G and R to the diffuse fraction D may be used in various exemplary embodiments in a known manner (as mentioned elsewhere herein) to determine the gloss value.

Figure 3:
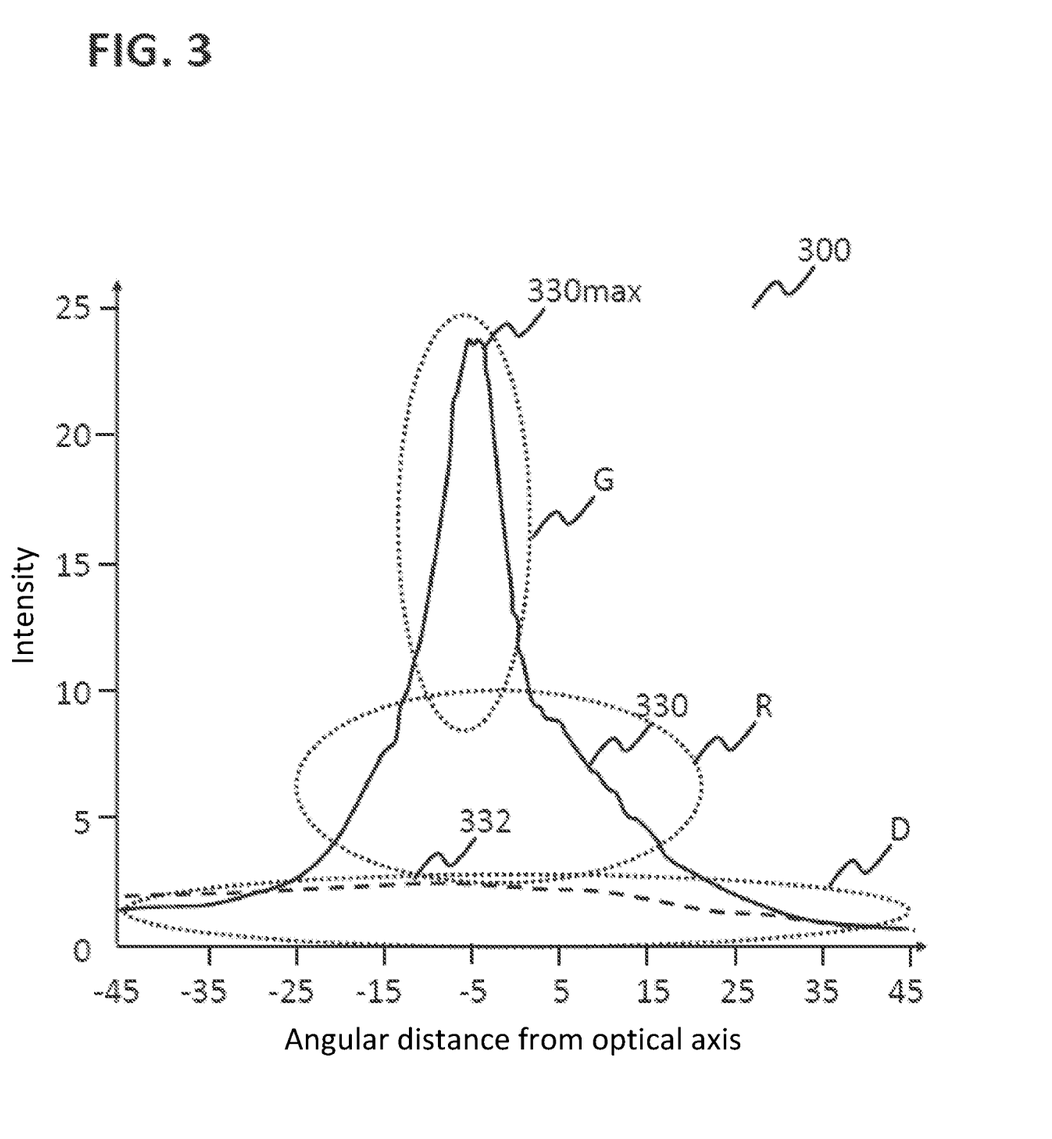

FIG. 3 shows a brightness curve 300, which is determined by applying a method to determine the gloss value of hair in various exemplary embodiments.

The course may be determined essentially along a direction in which the hairs 102H or hair sections run, for example as an average value averaged over all hairs or for a partial area, i.e. a part of the hairs 102H.

Light components which correspond to the light G reflected from the front, the light R reflected from the rear of the hair or the diffusely scattered light D are approximately marked in FIG. 3 by elliptical areas.

Software may be used in various exemplary embodiments for the determinations described above. Any software that provides the functionality described above may be used. In various exemplary embodiments, e.g. in a case where a smartphone or tablet is used to perform the method for determining a gloss value of hair, the software may be provided as an app.

A gloss value for the displayed hair 102H may be determined by examining the brightness values of the displayed hair 102H, e.g. by determining a plurality of brightness values of the hair 102H, and evaluating the brightness values, e.g. by the above mentioned method.

In various exemplary embodiments, e.g. by calculation and/or comparison with reference values provided, an absolute gloss value may be determined for the hair 102H, e.g. for the hair 102H in the hair examination area and/or for a hairstyle.

In various exemplary embodiments, a gloss value may be assigned to the brightness ratio, e.g. by comparison with reference values. The reference values may have been established in advance, e.g. by empirical data, and may be retrievable, e.g. as a reference database for the data processing device 104, e.g. stored in a memory of the data processing device 104, or retrievable, e.g. from a cloud.

The reference data may, for example, have a multi-stage gloss value scale, e.g. with at least two gloss values (e.g. from "very low" to "very high"), e.g. three to five gloss values, which has for each of the gloss values of the at least one measured value which may be determined by the determined plurality of different brightness values, e.g. from the brightness ratio of reflected (G+R) to diffuse (D) scatter.

In various exemplary embodiments, a maximum brightness value may be used as an alternative or in addition to the ratio of reflected and diffuse scattering. In order to reduce a fluctuation range, an arithmetic mean value of the highest about 5% of the brightness values may be used as the maximum brightness value.

The following table shows an exemplary relationship between brightness ratios and gloss values:

| Ratio of reflection (G + R) to diffuse scattering (D) | Gloss value |
|---|---|
| (G + R)/D ≤ 3 | 1 = slightly glossy |
| 3 < (G + R)/D ≤ 5 | 2 = moderately glossy |
| 5 < (G + R)/D (e.g. ≤ 7) | 3 = very glossy |

In various exemplary embodiments, the determination of the hair gloss value and/or the determination of the hair care product for gloss enhancement may be carried out directly using the data processing device 104.

In various exemplary embodiments, the determination of the hair gloss value and/or the determination of the hair care product for gloss enhancement may be carried out indirectly by the data processing device 104, for example, by the data processing device 104 being set up to process the digital image and/or the (brightness) values determined therefrom of an external data processing device, e.g. a cloud, which may be set up to determine the gloss value from the digital image and/or the (brightness) values determined therefrom and/or to determine the hair care product for gloss enhancement from the determined values and/or from the gloss value and to make it available to the device 100.

In various exemplary embodiments, images of user's hair may be taken from different directions, i.e. from different hair areas.

If only one image is taken, various exemplary embodiments may show the user's hair at the back of the head, as the back of the head typically has a suitable curvature. However, in various exemplary embodiments another hair area of the user may be used as the only hair area shown, provided it has the appropriate curvature.

In various exemplary embodiments, those areas with little or no hair, e.g. facial areas and/or background areas, may be eliminated in images 200, e.g. in a known manner, e.g. by applying a morphing filter. In other words, the hair display area, which may predominantly contain only hair, may be determined, and the image area that is not the hair display area may be discarded.

In various exemplary embodiments, based on a gloss value determined as described above for various exemplary embodiments, a hair care product, e.g. a hair care product suitable for the gloss value, may be determined.

The hair care product may be one of a group of hair care products of which it is known or expected that their suitability for hair care applications may depend on an initial gloss value of the hair, i.e. that they may be particularly suitable for hair with a given gloss value.

In various exemplary embodiments, the group of hair care products may include hair care products for the gloss enhancement of hair.

An assignment of gloss values and suitable hair care products, e.g. gloss enhancement products, may be provided as a given database, which may be based on empirical data, e.g. in a memory of the data processing device and/or in a cloud.

The suitable hair care products may include chemical product groups and/or specific product names under which the user could purchase them.

The method for determining a hair care product and/or a hair treatment recommendation may further include the initiation of an online ordering process of the determined hair care product and/or the provision of a reference where the determined hair care product is available.

The method may also include the initiation of an order process for individually manufactured hair care products.

More and more customers want a product that is individually tailored to their needs. This may be a product manufactured especially for the customer or a so-called "mass-customized" product. In the case of a mass-customized product, individualization may be achieved by varying a few features of a product that are decisive from the customer's point of view. Preferably, these mass-customized products are based on the concept of modularization, i.e. the product may be individually assembled from various modules/components.

There are often numerous interdependencies between the many different features/contents of a product, which can be expressed as "requirements" or "restrictions". In order to obtain a clear product definition, it may be advantageous to use a product configurator for the ordering process. This configurator helps the customer to select the characteristics/ingredients and points out of the permissible/non-permissible combinations of characteristics, whereby the latter may then not be selected.

For hair care products, the relevant product characteristics include in particular the chemical ingredients of the products, the physical properties of the products and the type of packaging of the products. With the help of a product configurator, for example, the selection of chemically and/or physically incompatible ingredients or the selection of ingredients unsuitable for the gloss value determined may be avoided. Conversely, the selection of suitable ingredients for the determined gloss value may be specified or suggested by the product configurator.

The hair care producers may be assigned to the gloss values at different levels, or conversely, the group of hair care products may be divided into a number of care levels, e.g. gloss enhancements levels, and gloss values for which the hair care producers of the respective gloss enhancements level may be suitable may be defined.

In the case of gloss enhancement products, different levels of gloss enhancement may be based on ingredients such as dimethicone (light gloss creation), apricot kernel oil (medium gloss creation) and/or phenyl trimethicone (strong gloss creation).

Accordingly, in various exemplary embodiments, a user may receive an exact product recommendation tailored to his initial hair gloss value, e.g. for increasing hair gloss, without having to carry out his own hair assessment, but rather, depending on the prerequisites, e.g. simply without further preparation (in the case of straight hair lying close to the head, aligned essentially parallel and suitably curved on the head), after shaping the hair to the head so that it has the appropriate curvature and is aligned essentially parallel to each other (in the case of hair, which is waved without manipulation) or after arranging the hair on an essentially cylindrical object, captures or has captured one or more pictures of his hair with his smartphone while illuminating the hair and has this picture evaluated by an app for determining a hair care product and/or a hair treatment recommendation.

In various exemplary embodiments, the initial gloss value for which a care product may be suitable for gloss enhancement may have a value from one of the multi-stage waviness scales described above. The hair care product for gloss enhancement may be one of a plurality of hair care products for gloss enhancement, wherein each of the plurality of hair care products for gloss enhancement may have an associated gloss enhancement level, and wherein determining a hair care product based on the determined gloss value may involve determining a hair care product with a higher gloss generation level for hair with a lower gloss value.

The following table shows an exemplary assignment of product recommendations for hair gloss values:

| Gloss value | Product recommendation |
| --- | --- |
| 1 = slightly glossy | Product 1 for strong gloss enhancement, containing phenyl trimethicone as a strong gloss enhancing ingredient (e.g. with a percentage of about 1% by weight) |
| 2 = moderately glossy | Product 2 for strong gloss enhancement, containing apricot kernel oil as a moderate to strong gloss enhancing ingredient (e.g. with a percentage of about 1% by weight) |
| 3 = very glossy | Product 3 for light gloss enhancement, containing dimethicone as a light gloss enhancing ingredient (e.g. with a percentage of about 1% by weight) |

In the table, the terms "Product 1", etc. may be general terms for the respective product group and/or representative of one or more product names under which the user could purchase the respective product.

The number of gloss levels, classifications of products, etc. should be taken as examples. The number of gloss levels may, for example, range from about 2 to about 20, e.g. between about 2 and about 4, e.g., as described above, about 3. A numerical value by which the gloss value is assigned may, in various exemplary embodiments, depend on the method used to determine the gloss (e.g., according to Reich-Robbins or Lefaudeux). Usually, the value range may extend from about 1 to about 20, for example, as shown above, from about 1 to about 7.

In various exemplary embodiments, other or additional gloss enhancements may be included in the product recommendation as an alternative and/or in addition to the above mentioned gloss enhancements, for example other known gloss enhancements, e.g. a product 1 for low gloss enhancement containing trisiloxane (e.g. with a percentage of about 1% by weight).

A result of the determination of the hair care product may be made available to the user, e.g. by the output device 106, e.g. displayed (e.g. by the smartphone display of the device 100, as exemplarily shown in FIG. 1B or another display device) or made accessible in another way, e.g. by voice output.

In various exemplary embodiments, the method for determining a gloss value of hair before and after applying a hair care product for gloss enhancement may be applied. Thus, the effectiveness of the gloss enhancement ingredient may be determined objectively.

In various exemplary embodiments, a hair treatment for gloss enhancement may be determined. This may include, for example, the recommendation to visit a hairdresser. In various exemplary embodiments, a booking process may be initiated directly via the software/app that determines the hair care product and/or the hair treatment recommendation. For this purpose, the contact data of hairdressers may be stored in the software/app and displayed to the user. In addition, the selection may be limited via filters, such as the postcode, for example. In various exemplary embodiments, an appointment booking may be directly made via the software/app. Alternatively, a hairdresser appointment may be booked via a separate software/app, such as Treatwell.

Figure 4:
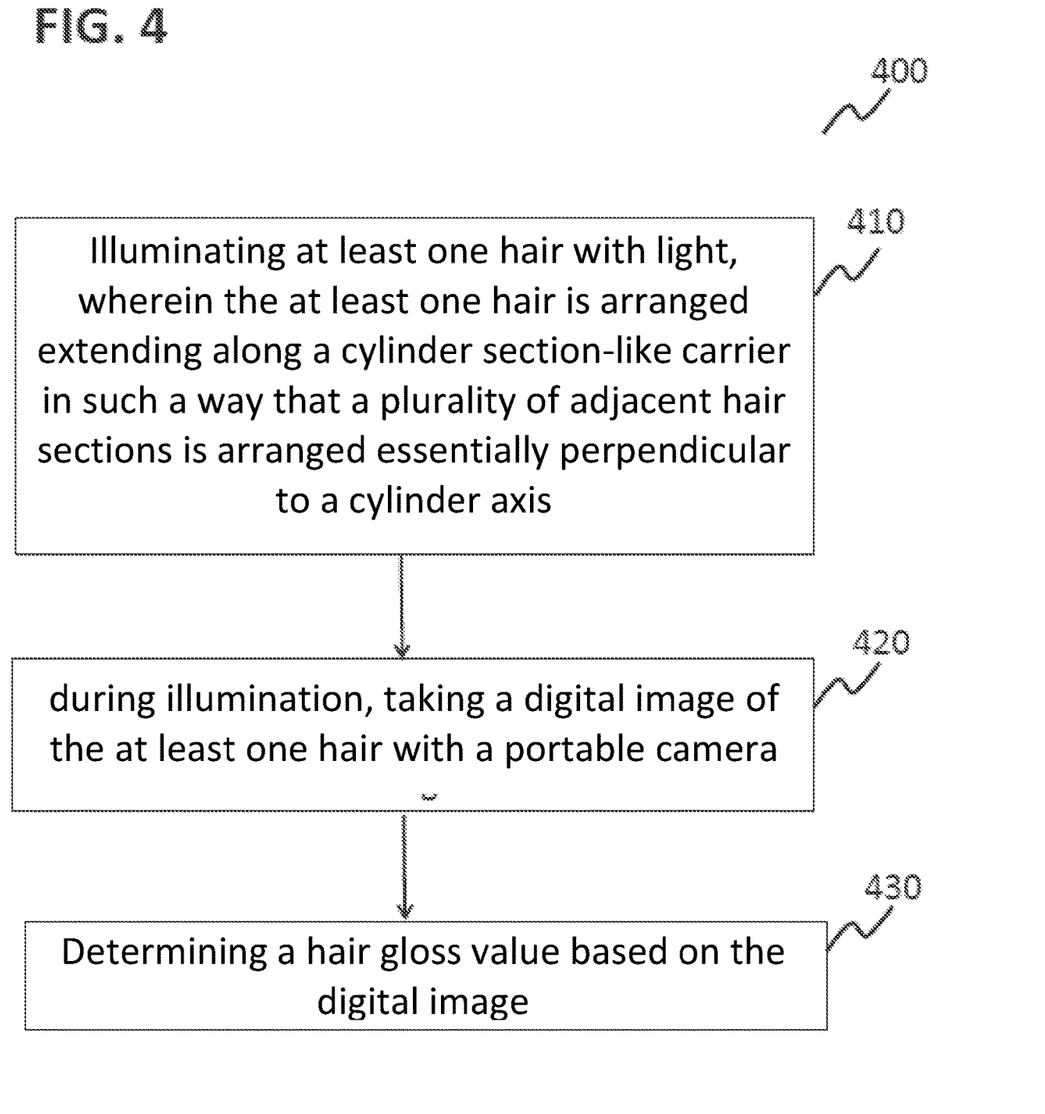

FIG. 4 shows a flowchart 400 of a method to determine a gloss value of hair according to different example embodiments.

In various exemplary embodiments, the method may comprise illuminating at least one hair with light, wherein the at least one hair is arranged to extend along a cylinder section-like carrier in such a way that a plurality of adjacent hair sections is arranged essentially perpendicular to a cylinder axis (in 410), during exposure, capturing a digital image of the at least one hair by a portable camera (in 420), and determining a gloss value of the hair based on the digital image (in 430).

Figure 5:
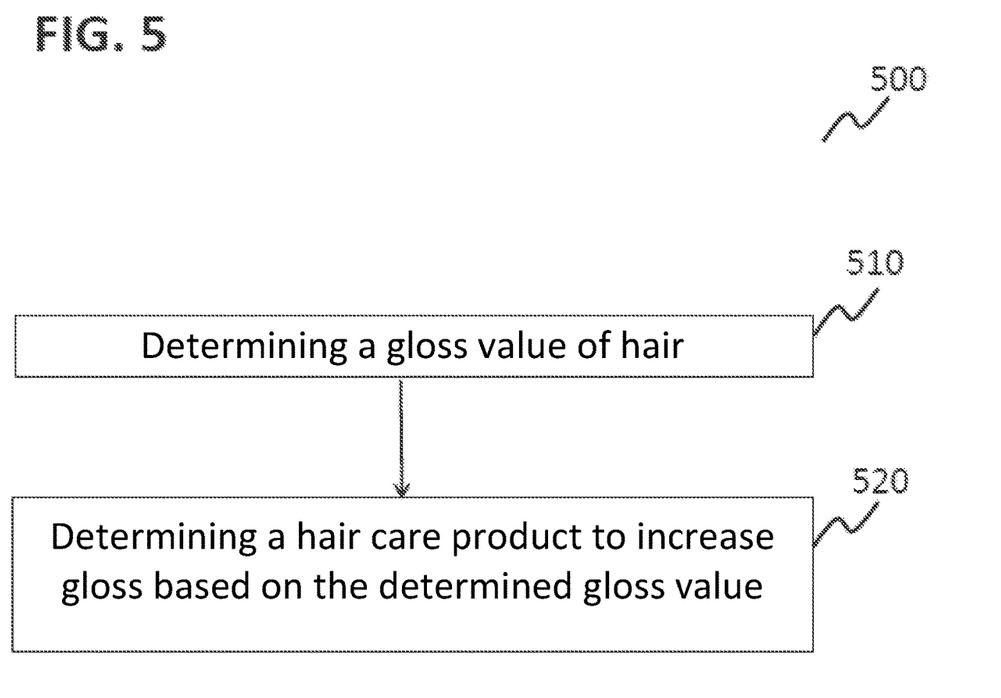
FIG. 5 is a flowchart of a method for determining a hair care product and/or hair treatment recommendation according to various exemplary embodiments.

FIG. 5 shows a flowchart 500 of a method for determining a gloss value of hair according to various exemplary embodiments.

In various exemplary embodiments, the method may be used to determine a gloss value of hair samples (in 510), for example according to various exemplary embodiments described above, and to determine a hair care product and/or a hair treatment recommendation for gloss enhancement based on the determined gloss value (in 520).

Further advantageous designs of the method result from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a suggested hair care product for gloss enhancement of hair, comprising:
    illuminating at least one hair with light, wherein said at least one hair is arranged to extend along a cylinder support with a plurality of adjacent hair sections arranged perpendicular to a cylinder axis;
    during illumination, capturing a digital image of the at least one hair by a portable camera;
    determining, via a processor, a gloss value of the hair from a multi-stage gloss scale based on a brightness of the digital image, by examination of the digital image that includes transforming the digital image into a color space that includes a brightness parameter;
    determining, via the processor, the suggested hair care product for gloss enhancement from a plurality of hair care products for gloss enhancement, wherein each of the plurality of hair care products for gloss enhancement has an associated gloss enhancement level, and wherein determining of the suggested hair care product for gloss enhancement is based on the determined gloss value, and wherein a hair care product with a higher gloss generation level is suggested for hair with a lower gloss value; and
    outputting, via an output device, the suggested hair care product for gloss enhancement, via instructions provided to the output device by the processor;
    wherein:
        the light is linearly polarized, with an oscillation plane of the polarized light running along the cylinder axis;
        the step of determining the gloss value of the hair comprises determining the gloss value of the hair based on a brightness ratio of reflected to diffuse scatter of the digital image, and based on a table of known values of gloss values of hair correlated with brightness ratios of reflected to diffuse scatter; and
the outputting comprises outputting, via instructions provided by the processor to a display screen of a smart phone, the suggested hair care product for gloss enhancement.

2. The method according to claim 1, wherein the determining of the gloss value of the hair further comprises determining a maximum brightness value in a hair region of the digital image and assigning the maximum brightness value to a gloss value.

3. The method according to claim 1, wherein the determining of the gloss value of the hair further comprises determining a gloss area in a hair region of the digital image, summing gloss brightness values of all image elements in the gloss area, and assigning the sum to a gloss value.

4. The method according to claim 1, further comprising: positioning the portable camera so that an angle between a main direction from which the light illuminates the hair and an optical axis of the portable camera has an angle of approximately 45°.

5. The method according to claim 1, wherein the illuminating of the at least one hair is effected by a light source which together with the portable camera is part of an integrated portable device.

6. The method according to claim 1, further comprising: arranging the hair on the cylindrical support.

7. The method according to claim 1, wherein the digital image is parameterized in a color space having brightness as a parameter.

8. The method according to claim 1, further comprising: initiating an online ordering process of the suggested hair care product and/or providing an indication of where the identified hair care product is available.

9. A device for determining a suggested hair care product for gloss enhancement of hair, comprising:
a light source for illuminating at least one hair with light, wherein the at least one hair is arranged extending along a cylinder support with a plurality of hair sections arranged side by side are perpendicular to a cylinder axis;
a portable camera for capturing a digital image of the at least one hair during illumination;
an output device; and
a portable electronic data processing device configured to:
determine a gloss value of the hair from a multi-stage gloss scale based on a brightness of the digital image by examination of the digital image that includes transforming the digital image into a color space that includes a brightness parameter;
determine the suggested hair care product for gloss enhancement from a plurality of hair care products for gloss enhancement, wherein each of the plurality of hair care products for gloss enhancement has an associated gloss enhancement level, and wherein determining of the suggested hair care product for gloss enhancement is based on the determined gloss value, and wherein a hair care product with a higher gloss generation level is suggested for hair with a lower gloss value; and
provide instructions for outputting, to the output device, the suggested hair care product for gloss enhancement;
wherein the output device is configured to output the suggested hair care product for gloss enhancement in accordance with the instructions provided to the output device by the processor;
wherein the light emitted from the light source is linearly polarized, with an oscillation plane of the polarized light running along the cylinder axis; and
wherein the portable electronic data processing device is configured to:
determine the gloss value of the hair based on a brightness ratio of reflected to diffuse scatter of the digital image, and based on a table of known values of gloss values of hair correlated with brightness ratios of reflected to diffuse scatter; and
provide the instructions for outputting, to a display screen of a smart phone, the suggested hair care product for gloss enhancement.

10. The device according to claim 9, wherein the portable camera and the data processing device are part of an integrated portable device.

11. The device according to claim 10, wherein the light source is part of the integrated portable device.

12. The device according to claim 10, wherein the integrated portable device comprises a smartphone or tablet.

13. The method of claim 1, wherein the step of determining the gloss value of the hair further comprises determining the gloss value of the hair based on a maximum brightness value of the digital image.

14. The method of claim 1, wherein the outputting further comprises outputting, via instructions provided by the processor to a loudspeaker, the suggested hair care product for gloss enhancement.

* * * * *